United States Patent [19]

Salyer

[11] Patent Number: 4,811,632

[45] Date of Patent: Mar. 14, 1989

[54] METHOD OF PRODUCING AN ACETABULAR REAMER CUP

[75] Inventor: Paul E. Salyer, Warsaw, Ind.

[73] Assignee: Othy, Inc., Warsaw, Ind.

[21] Appl. No.: 825,992

[22] Filed: Feb. 4, 1986

[51] Int. Cl.[4] .................. B21K 21/00; B23D 73/04
[52] U.S. Cl. ...................... 76/101 A; 76/24 R
[58] Field of Search .......... 76/101 R, 101 SM, 101 A, 76/24 R, 13; 29/78

[56] References Cited

U.S. PATENT DOCUMENTS 4,116,200  9/1978  Braun et al. .................. 29/78

FOREIGN PATENT DOCUMENTS 666621  2/1952  United Kingdom .......... 76/101 SM

*Primary Examiner*—Roscoe V. Parker
*Attorney, Agent, or Firm*—Lundy and Walker

[57] ABSTRACT

A method for making an acetabular reamer cup and an acetabular reamer cup made thereby. The method comprises the steps of fabricating a bowl-shaped cup-blank having an outer surface, an inner surface and a rim, perforating a plurality of holes through the cup-blank, the holes each being surrounded by a margin, deforming outwardly a cutting portion of the margin of each of the holes, smoothing the outer surface of the cup-blank to sharpen the deformed cutting portions, raising cutting edges from the cutting portions and removing the rim. The cutting edges are disposed to cut upon rotation of the acetabular reamer. The cup manufactured by this method is preferred because of its improved strength and consistently superior cutting edges.

16 Claims, 3 Drawing Sheets

METHOD OF PRODUCING AN ACETABULAR REAMER CUP

BACKGROUND OF THE INVENTION

The present invention pertains to acetabular reamers and more particularly to acetabular reamer cups.

Acetabular reamers are used by surgeons to prepare pelvis bones for insertion of artificial hip joints. An acetabular reamer is rotated to cut a cavity into the bone into which the socket portion of the artificial hip joint can be inserted. Dimensions and shape of the cavity cut are critical as the tolerances between the cavity and the socket portion of an artificial hip joint must be small to ensure proper function. This is especially true with the newly available "cementless" hip joints. Before, "cementless" hip joints, the socket portion of the joint was cemented into the cavity in the pelvis bone. In the "cementless" joint, the socket portion is frictionally fit into the cavity, placing new importance upon accurate cavity dimensions and tolerances.

In past methods of making acetabular reamer cups, holes in the cup were countersunk from the inside and then a part of the edge of the hole was pushed up and subsequently hand sharpened. This process is slow and very dependent on the skill of the individual workman sharpening the edges. The acetabular reamer cup produced by that method has edges sharpened to a double bevel and as a result, the edges stay sharp only a relatively short period of time.

It is therefore highly desirable to provide an improved method for producing an acetabular reamer cup and to provide an improved cup produced by that method.

It is also highly desirable to provide an improved method for producing an acetabular reamer cup which does not require the countersinking of holes and to provide an improved cup produced by that method which has more strength and improved cutting edges.

It is further highly desirable to provide a method for producing an improved acetabular reamer cup that does not require hand sharpening of edges and to provide an improved cup produced by that method which has more strength and improved cutting edges.

It is further highly desirable to provide an improved method for producing an acetabular reamer cup that is faster and more economical than past methods and to provide an improved cup produced by that method which has more strength and improved cutting edges.

It is yet also highly desirable to provide an improved method for producing an acetabular reamer cup that has single bevel cutting edges and to provide an improved cup produced by that method which has more strength and improved cutting edges.

It would finally be highly desirable to provide an improved method for producing an acetabular reamer cup and to provide an improved cup produced by that method which meet all of the above desired features.

SUMMARY OF THE INVENTION

It is an object of the invention to provide an improved method for producing an acetabular reamer cup and to provide an improved cup produced by that method.

It is another object of the invention to provide an improved method for producing an acetabular reamer cup which does not require the countersinking of holes and to provide an improved cup produced by that method which has more strength and improved cutting edges.

It is yet another object of the invention to provide a method for producing an improved acetabular reamer cup that does not require hand sharpening of edges.

It is still a further object of the invention to provide an improved method for producing an acetabular reamer cup that is faster and more economical than past methods and to provide an improved cup produced by that method which has more strength and improved cutting edges.

It is yet also another object of the invention to provide an improved method for producing an acetabular reamer cup that has single bevel cutting edges and to provide an improved cup produced by that method which has more strength and improved cutting edges.

It is still another object of the invention to provide an improved method for producing an acetabular reamer cup and to provide an improved cup produced by that method which meet all of the above desired features.

In the broader aspects of the invention there is provided a method for making an acetabular reamer cup for use with an acetabular reamer. The method includes the steps of fabricating a bowl-shaped cup-blank having an outer surface, an inner surface and a rim, perforating a plurality of holes through the cup-blank, the holes each being surrounded by a margin, deforming outwardly a cutting portion of the margin of each of the holes, smoothing the outer surface of the cup-blank to sharpen the deformed cutting portions, and raising the cutting edges from the cutting portions and removing the rim. The cutting edges are disposed to cut upon rotation of the acetabular reamer. The cup manufactured by this method is preferred because of its improved strength and consistently superior cutting edges.

BRIEF DESCRIPTION OF THE DRAWINGS

The above-mentioned and other features and objects of this invention and the manner of obtaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
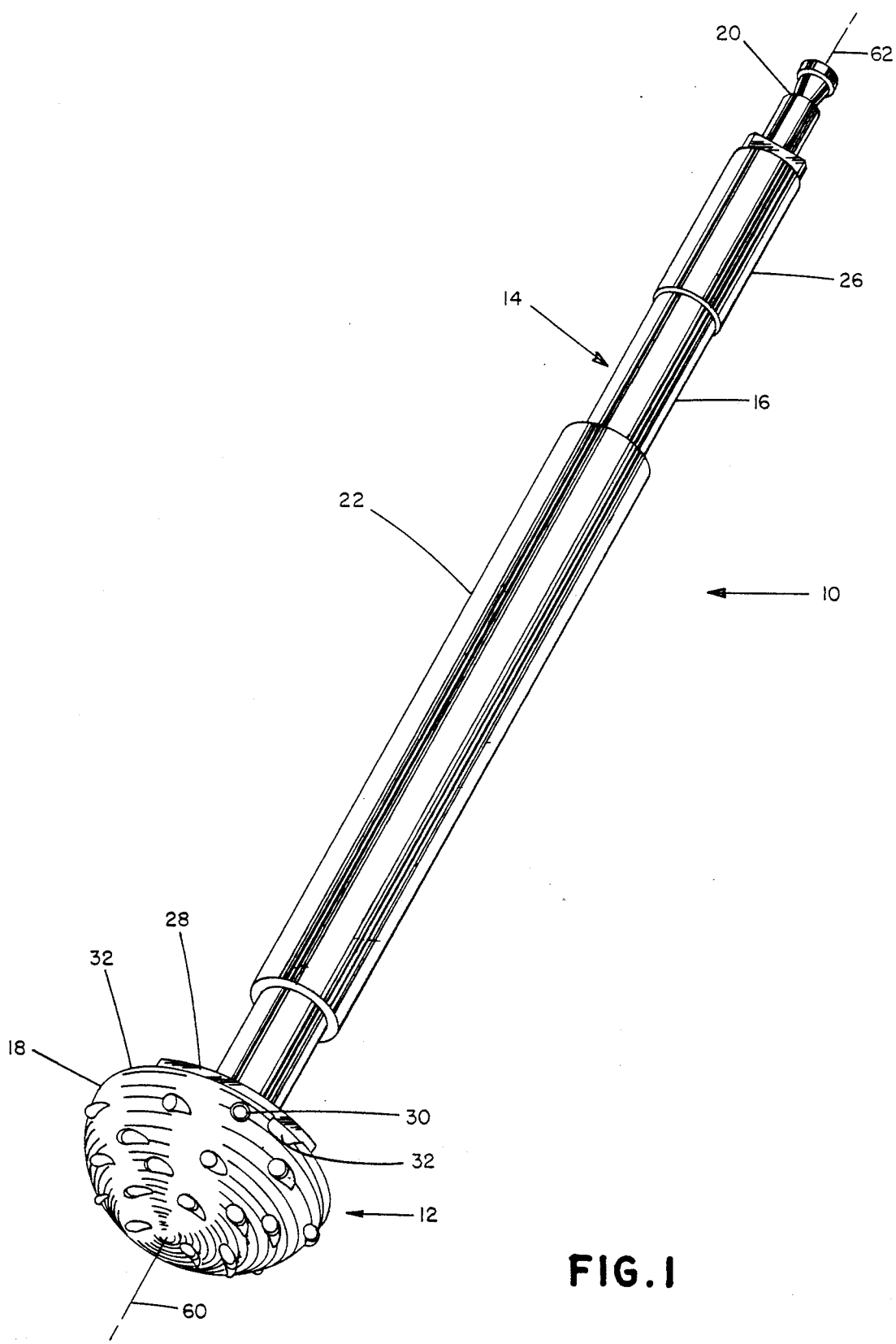
FIG. 1 is a perspective view of an acetabular reamer including the acetabular reamer cup of the invention.
Figure 2:
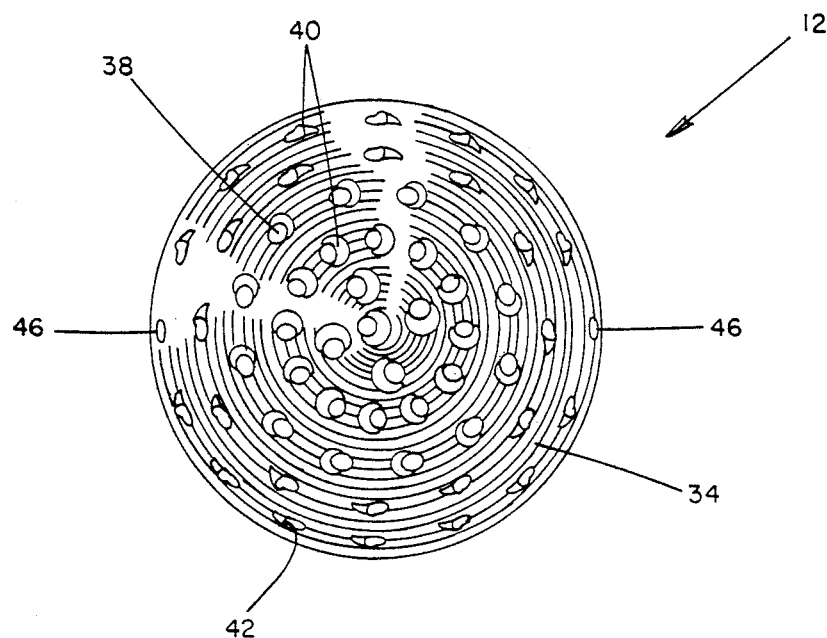
FIG. 2 is a top plan view of the acetabular reamer cup of the invention.
Figure 3:
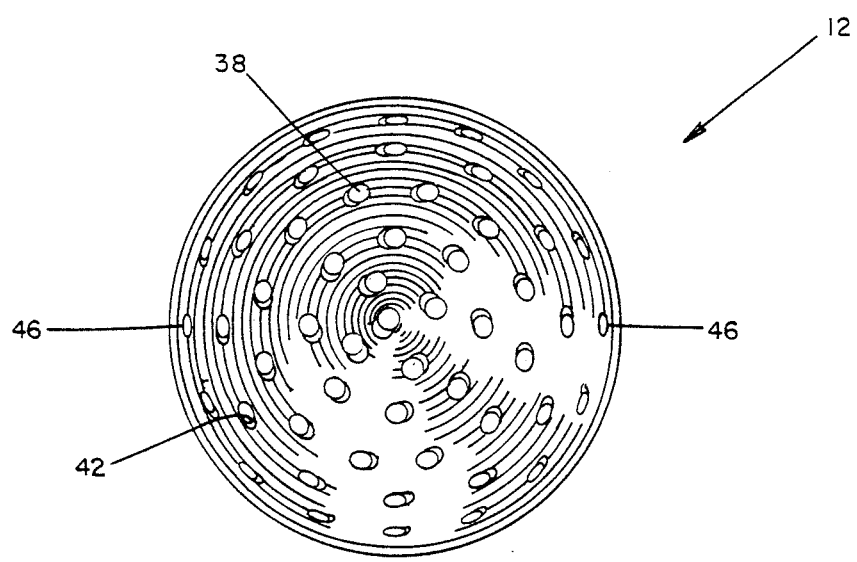
FIG. 3 is a bottom plan view of the acetabular reamer cup of the invention.
Figure 4:
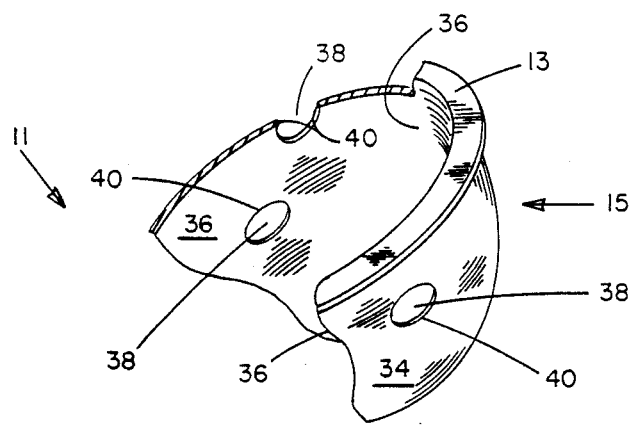
FIG. 4 is a fragmentary cross-sectional view of a perforated cup-blank following the perforating step of the method of the invention.
Figure 5:
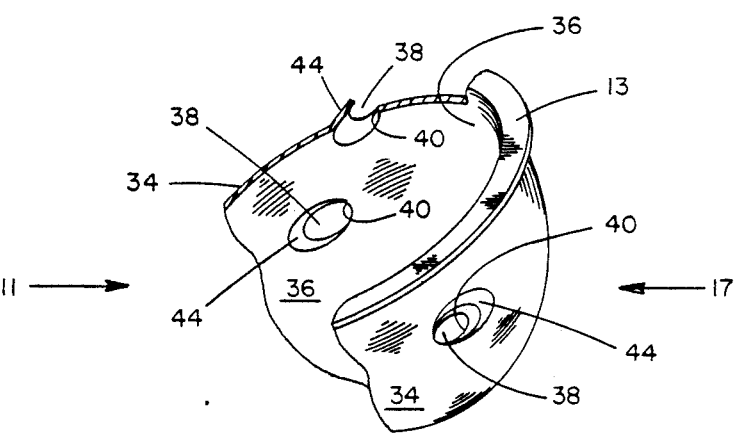
FIG. 5 is a fragmentary cross-sectional view of a relieved cup-blank following the deforming step of the method of the invention.
Figure 6:
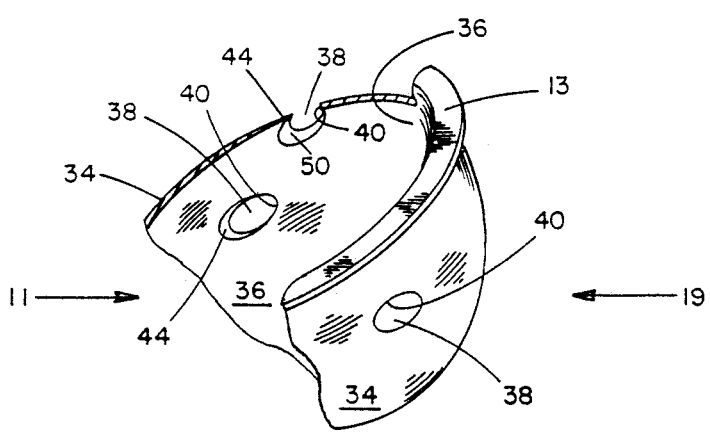
FIG. 6 is a fragmentary cross-sectional view of a smoothed cup-blank following the smoothing step of the method of the invention.
Figure 7:
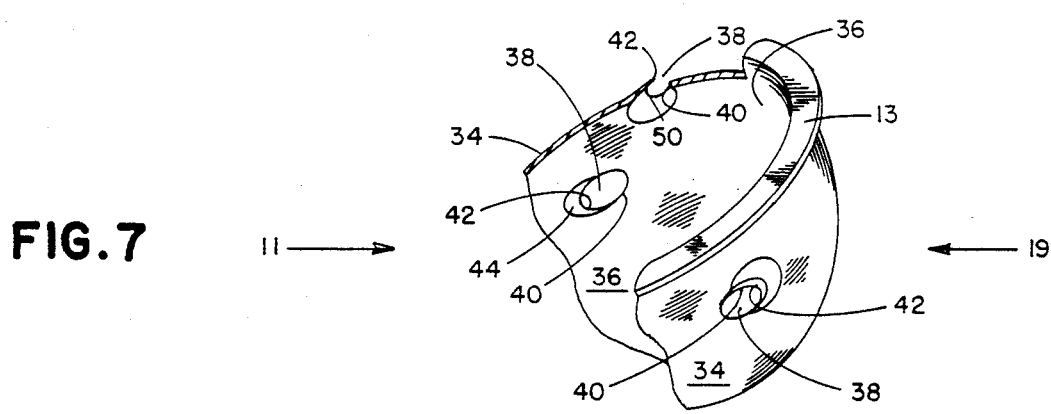
FIG. 7 is a fragmentary cross-sectional view of the acetabular reamer cup of the invention following the raising step of the method of the invention.

Acetabular reamer 10 has an acetabular reamer cup 12 and a shaft assembly 14. The shaft assembly 14 has a shaft 16, which has a chuck end 20 and a cup end 18. A handle 22 free to slide on the shaft 16 is positioned on shaft 16 between cup end 18 and a stop 26. See FIGS. 1, 2 and 3.

The cup end 18 of the acetabular reamer 10 has a cylindrical surface 28 coaxial with the shaft 16 on which cup 12 is removably secured by means of a pair of pins 30 extending through holes 46 therein, one pin 30 being retractable. Surface 28 has a base 28 which extends transversly of shaft 14. The cup 12 is retained by pins 30 against base 32 of the surface 28.

In other embodiments of the invention, the cup 12 could be mounted to the shaft assembly 14 by engaging threads or discrete fasteners or other equivalent means.

The cup 12 has an axis 60 which is coincident with the axis of rotation 62 of the shaft assembly 14 when the cup 12 is assembled on the shaft assembly 14.

The cup 12 of acetabular reamer 10 is generally bowl-shaped and preferably hemispherical, however, the invention is not limited to a hemispherical bowl-shaped cup 12 but may include bowl-shaped cups of other portions of a sphere or cups with the shape of other surfaces of revolution. The cup 12 is made of a material capable of holding a sharpened edge through a reasonable period of use. Stainless steel is one of the materials that is suitable for the cup 12.

In the method of the invention, illustrated in FIGS. 4, 5, 6 and 7, a bowl-shaped cup-blank 11 is first fabricated. This may be done by drawing or by any equivalent method. In this application, precursors of the cup 12 will be referred to generally as a cup-blank and specifically as modified forms of that term, such as for example; "solid cup-blank 11." In a specific embodiment of the invention, the bowl-shaped solid cup-blank 11 includes a peripheral lip 13 which increases the strength of cup-blank 11 and provides a means by which the cup-blank 11 may be held during fabrication during later steps. In this embodiment, the peripheral lip 13 is removed before the acetabular reamer cup 12 is completed.

After the solid cup-blank 11 is fabricated the solid cup-blank 11 is perforated with a plurality of holes 38 each surrounded by a margin 40. This yields a perforated cup-blank 15. If the holes 38 are formed by a method that produces burrs, the perforate cup-blank 15 must be deburred. The holes may be punched or drilled or formed by other equivalent means. It is convenient to make the holes 38 round, however, this method is not limited to round holes. In a specific embodiment of the method of the invention, the holes 38 are cut in a pattern which defines a spiral shape upon rotation of the cup 12 about its axis 60. See FIG. 4.

A cutting portion 44 of the margin 40 of each hole 38 is subsequently deformed outwardly to yield a relieved cup-blank 17 and result in a cutting portion 44 which is curved generally in the direction of the surfaces of the cup-blank with a radius or a minor axis of a non-circular arc shorter than the radius or minor axis of the cup-blank 11 as determined by the deformation and curved generally tangentially of the cup-blank surfaces as determined by the curvature of the margin 40 prior to deformation. In a specific embodiment, the cutting portions 44 are each individually deformed outwardly and this is repeated for every hole 38. See FIG. 5.

In the specific embodiment of the invention described herein, the cutting portions 44 each extend over a substantial portion of a respective margin 40, but substantially less than the entire margin 40. In specific embodiments of the invention, the cutting portions 44 extend between 200° and 270° around the holes 38. In a specific embodiment of the invention, the cutting portions 44 extend about 240° around the holes 38.

The outer surface 34 of the relieved cup-blank 17 is subsequently smoothed. This yields the smoothed blank 19. The smoothing may be performed by sanding or grinding or any equivalent procedure. This removes a part of each cutting portion 44 and sharpens the remaining part of each cutting portion 44, forming a sharpened bevel 50. In a specific embodiment of the invention, the appearance of the outside surface 34 of the smoothed cup-blank 19 is essentially the same as the appearance of the perforated cup-blank 15, since the size of the holes 38 remains about the same. See FIG. 6.

The cutting edges 42 are subsequently raised from the cutting portions 44. This yields the acetabular reamer cup 12 of the invention. See FIG. 7. In a specific embodiment, the cutting edges 42 are each individually raised and this is repeated for each cutting edge 42. In raising the cutting edges 42, the shapes of the holes 38 are changed, in an embodiment in which the holes are initially circles, to a generally elliptical shape and the cutting edges 42 are curved generally in the direction of the surfaces of the cup-blank with a radius or a minor axis of a non-circular arc shorter than the radius or minor axis of the cup-blank 11 as determined by the deformation and curved generally tangentially of the cup-blank surfaces as determined by the curvature of the margin 40 prior to deformation. In a specific embodiment of the invention, the height of the cutting edges 42 from the outside surface 34 of the cup 12 is the same within a selected tolerance. In that embodiment, the tolerance is from about 0.034 to about 0.046. After a cutting edge 42 is raised, its bevel 50 protrudes from the outer surface 34. The cutting edges 42 do not need additional sharpening before use. The improved method of the invention, in fact, completely eliminates previous chamfer and hand-sharpening operations and produces a single bevel cutting edge 42. The cutting edges 42 will cut any substrate against which the cup 12 is rotated. The cutting edges 42 are improved over the cutting edges of prior acetabular reamers as they are consistently sharper, are more consistent when compared one to another, and stay sharper than the cutting edges of prior acetabular reamers.

Comparing the acetabular reamers of the invention with prior acetabular reamers, a cavity can be formed in a pelvic bone with smaller tolerances than heretofore possible because of the greater consistency between cutting edges 42. With the acetabular reamer of the invention, ±0.006 inch tolerances can be achieved, whereas heretofore normal tolerances were −0.010 inches. Such tolerances are desired with the new "cementless" hip joints.

Additionally, the improved sharpness of the cutting edges 42 can be documented by comparison testing using the following:

TESTING EQUIPMENT

Pattern mahogany in squares approximately 2.75" with a 0.500" pilot hole.

Enco milling and drilling machine Model No. 91034.

The tester is belted to operate at 300 RPM's.

May be purchased from: Enco Manufacturing Co. Chicago, Ill.

Dial indicator with a travel from 0.001"–1.00".

A time such as a West Bend electronic time, Cat. No. 4000.

May be purchased from:

The West Bend Company
West Bend, WI 53095

TESTING PROCEDURE

Select a shaft assembly 14 that best fits the cup needing testing.

Placing cup on selected shaft assembly 14, use a locking pin and secure cup to the shaft assembly 14

Select proper mahogany block for test. If testing a 40-45 MM cup, use a new block with a pilot hole. If testing a 46 MM or larger cup, a block may be reused. For example If a mahogany block has been used to test a 54 MM cup, it can be used to test a 56 MM cup, etc. In all cups the entire spherical cutting path will be tested.

Place the mahogany block in the vise located at the base of the sharpness tester, and tighten the vise until the mahogany block is firm in place. Lowering the shaft assembly 14 down on the top of the block, center the top of the cup to the pilot hole by moving the adjustment handles left, right, back or forward.

Using the adjustment arm to move the base up and down, set the dial on zero.

Set the timer for a period of 5 seconds for any cup 50 MM or smaller; 7 seconds for 51 MM to 59 MM, and 10 seconds for grater cups 60 MM and up.

Set the timer according to the cup size and start your tester by turning the switch to the ON position. The switch is located on the top left-hand side of the tester. Turn the switch to the OFF position when the time has expired.

Refer to the dial indicator for depth of cut.

A minimum cut of 0.350" shall be acceptable.

Prior art cutting edges and edges 42 are compared in the following table:

| Rim Size | Prior Art | | Cutting Edges 42 | |
| --- | --- | --- | --- | --- |
| 42 | 7 seconds | .460" .420" | 5 seconds | .550" Cup Bottomed Out[1] |
| 44 | 7 seconds 5 seconds | .405" .359 | 5 seconds | .420" Cup Bottomed Out[1] |
| 48 | 5 sec. | .150" | 5 sec. | .425" |
| 56 | 7 sec. | .045" | 7 sec. | .500" |
| 58/57 | 7 sec. | .145" | 7 sec. | .505" |

[1]Cup fills with compressed wood shavings and won't cut anymore.

In a specific embodiment of the invention, cutting edges 42 are each raised from a substantial part, but less than an entire respective cutting portion 44. In specific embodiments of the invention the cutting edges 42 extend from about 188° to about 192° around the hole 38. In a specific embodiment of the invention the cutting edges extend around about 190° around the hole 38. In a specific embodiment of the invention in which the holes 38 are arranged in a pattern which forms a spiral upon rotation of the cup 12 about its axis 60, the cutting edges 42 are arranged on margins 40 of the holes 38 to cut the spiral pattern defined by rotation of the head 12 about its axis 60. In other specific embodiments, the cutting edges 42, can be arranged on margins 40 to cut in other directions, for example, the direction of the rotation of the cup 12.

The acetabular reamer cup 12 produced by the method of the invention is used by connecting it to the shaft assembly 14 of an acetabular reamer 10 and connecting the shaft to a powered drill. The cup 12 is pressed against the pelvis of a patient while it is rotating and a cavity is cut for implantation of the artificial hip joint.

While a specific embodiment of the invention has been shown and described herein for purposes of illustration, it is desired that the protection afforded by any patent which may issue upon this application not be limited strictly to the disclosed embodiments; but that it extend to all structures and arrangements which contain the essence of the invention and which fall fairly within the scope of the claims which are appended hereto:

What is claimed is:

1. A method for making an acetabular reamer cup for an acetabular reamer comprising the steps of: fabricating a bowl-shaped cup-blank having outer and inner bowl-shaped surface, perforating a plurality of holes through said cup-blank, said holes each being surrounded by a curved margin, deforming outwardly of one of said surface a cutting portion of said margin of each of said holes, said cutting portions being curved outwardly of said one surface, smoothing said one surface of said cup-blank to sharpen said cutting portions, and raising curved cutting edges from said cutting portions outwardly of said one surface, said cutting edges also being curved tangentially of said one surface and disposed to cut upon rotation of said acetabular reamer.

2. The method of claim 1 wherein said deforming step further comprises the steps of individually deforming outwardly a cutting portion of said margin of one of said holes, and repeating said individually deforming step for every other hole.

3. The method of claim 1 wherein said raising step further comprises the steps of individually raising a cutting edge from one said cutting portions, and repeating said individually raising step for every other cutting portion.

4. The method of claim 1 wherein said cup-blank has a peripheral rim, further comprising the step of removing said peripheral rim.

5. The method of claim 1 further comprising the step of deburring said holes.

6. The method of claim 1 wherein the height of all said cutting edges from said outside surface is about essentially the same.

7. The method of claim 1 wherein the height of all said cutting edges from the rest of said outside surface is within ±0.006 inches.

8. The method of claim 1 wherein each said cutting portion extends between 238° and 242° around a respective one of said margin.

9. The method of claim 1 wherein said cutting portions extend about 240° around a respective one of said margins.

10. The method of claim 1 wherein each said cutting edge extends between 188° and 192° around a one of respective said margins.

11. The method of claim 1 wherein said cutting edges each extend about 190° around a respective one of said margins.

12. The method of claim 1 wherein said cutting edges are oriented to cut a spiral upon rotation of said acetabular reamer cup.

13. The method of claim 1 wherein said holes in said cup-blank are generally circular following said perforating step and said holes are generally elliptical following said raising step.

14. The method of claim 1 wherein the number of cutting edges is equal to the number of holes.

15. The method of claim 1 wherein the cutting portions of said margins and said cutting edges are each curved generally in the direction of said outer and inner surfaces of said cup-blank and have a tighter curve than said cup-blank as determined by said deforming and said raising, respectively.

16. The method of claim 1 wherein said cutting edges and said cutting portions of said margins are curved in a direction generally tangentially of said inner and outer surfaces of said cup-blank as determined by the shape of said margins prior to said deforming.

* * * * *